United States Patent [19]

Kaasenbrood et al.

[11] 3,936,500

[45] Feb. 3, 1976

[54] PROCESS FOR PREPARING UREA

[75] Inventors: Petrus J. C. Kaasenbrood; Johannes D. M. Verstegen, both of Sittard, Netherlands

[73] Assignee: Unie Van Kunstmestfabrieken, B.V., Utrecht, Netherlands

[22] Filed: June 12, 1973

[21] Appl. No.: 369,391

[30] Foreign Application Priority Data
June 12, 1972 Netherlands.................... 7207940

[52] U.S. Cl............................................. 260/555 A
[51] Int. Cl.² ..................................... C07C 126/00
[58] Field of Search ............................... 260/555 A

[56] References Cited
UNITED STATES PATENTS

| | | | |
|---|---|---|---|
| 3,356,723 | 12/1967 | Kaasenbrood | 260/555 A |
| 3,544,628 | 12/1970 | Hsu | 260/555 A |

Primary Examiner—James O. Thomas, Jr.
Assistant Examiner—A. Siegel
Attorney, Agent, or Firm—Cushman, Darby & Cushman

[57] ABSTRACT

Ammonium carbamate is decomposed and removed in the form of its gaseous components by contacting a urea synthesis solution comprising the carbamate with a stripping gas, such as carbon dioxide, the countercurrent stripping conducted at adiabatic conditions in the stripper unit. Urea synthesis solution to be treated is supplied at higher pressures and temperatures, at least 205°C and at a pressure of at least 225 atm. Conveniently, the decomposition of the ammonium carbamate and the removal of the liberated gases are carried out at these temperatures and pressures so that the stripper is operative under the same conditions as well.

4 Claims, 1 Drawing Figure

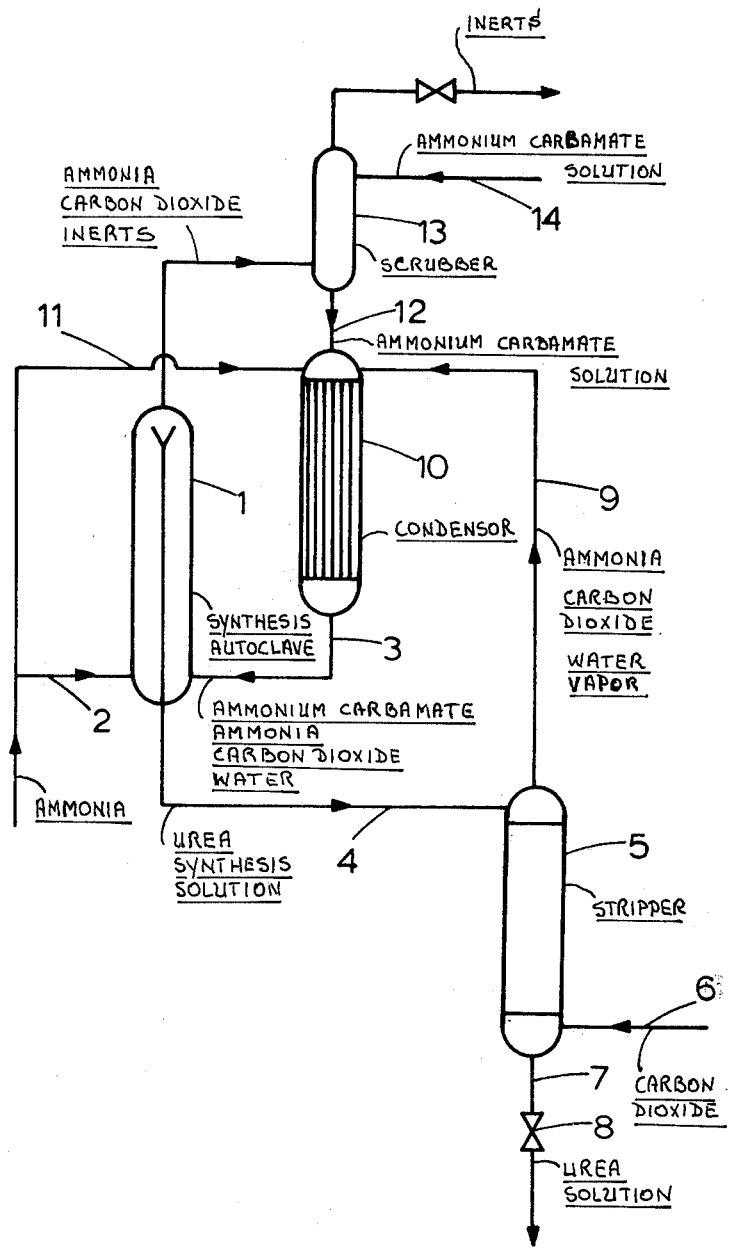

PROCESS FOR PREPARING UREA

BACKGROUND OF THE INVENTION

It is known that the preparation of urea from ammonia and carbon dioxide is in two steps, via the intermediate product ammonium carbamate; under the usual conditions of temperature and pressure the conversion of ammonia and carbon dioxide into ammonium carbamate according to the exothermic reaction:

$$2 NH_3 + CO_2 \rightleftarrows NH_2COONH_4 + a \text{ kcal}$$

is practically complete, but the conversion of the ammonium carbamate into urea according to the endothermic reaction $$NH_2COONH_4 \rightleftarrows CO(NH_2)_2 + H_2O - b \text{ kcal}$$

is only a partial one.

Synthesis pressures used in modern processes for preparation of urea are between 125 and 200 atm. and the synthesis temperatures used are between 180° and 200°C. These temperatures are in agreement with the findings of E. Otsuka, who investigated the conversion of ammonia and carbon dioxide into urea at different temperatures and molar ratios of $H_2O$ to $CO_2$ and found for each $H_2O$ to $CO_2$ ratio that the equilibrium conversion passes through a maximum at approximately 190°C. See Hydrocarbon Processing, June 1970, pages 111–115.

In order to increase the degree of conversion according to another known expedient, the urea synthesis is carried out in the presence of an excess quantity of ammonia. The solution obtained during the synthesis therefore contains, in addition to urea and water, non-converted ammonium carbamate and free $NH_3$. The ammonium carbamate and free ammonia should be removed from the solution before the urea solution can be concentrated and be processed into a salable end product.

According to the process described in U.S. Pat. No. 3,356,723, the non-converted ammonium carbamate and free $NH_3$ are removed by subjecting the urea synthesis solution, under pressure, to a countercurrent stripping treatment with gaseous carbon dioxide, in which the ammonium carbamate is decomposed into $NH_3$ and $CO_2$, with expulsion of a gaseous mixture of $NH_3$, $CO_2$ and $H_2O$. This gas mixture is condensed and returned as an ammonium carbamate solution to the urea synthesis zone. The disclosure of U.S. Pat. No. 3,356,723 in the name of Kaasenbrood, one of the coinventors herein, is hereby incorporated by reference to the extent necessary to fully describe the present invention.

The decomposition of the ammonium carbamate and the expulsion of the ammonia and the carbon dioxide are effected in the stripping process by reduction of the partial pressure of one of the two reaction components with the aid of the stripping gas and with the addition of heat. The decomposition can be hastened by using a pressure as low as possible at which the stripping treatment takes place. However, condensation of the gases discharged from the stripping zone should take place at as high a pressure as possible in order to assure the ammonium carbamate formation at as high a temperature as possible, so that there are more possibilities of applying the liberated heat and, also, that the ammonium carbamate is returned to the urea synthesis zone with as little water as possible — a desirable factor in view of the detrimental influence of water on the conversion to urea. For these reasons the condensation is carried out at the pressure at which the urea synthesis takes place so that there is only a small pressure differential, if any, between the condenser and the urea synthesis zone.

The gas mixture discharged from the stripping zone, which as mentioned, contains water in addition to ammonia and carbon dioxide, can only be compressed if special measures are taken to avoid formation of liquid or solid phases in the compressor and in the lines. Moreover, a particularly high amount of energy is needed for driving the compressors. In practice, therefore, the stripping treatment is carried out at the same pressure as the condensation and the synthesis. Actually, this pressure is determined by the maximum temperature level at which the heat required for the stripping treatment can still be supplied without hydrolysis of the urea formed and formation of biuret occurring to an unacceptable degree.

Further, to minimize or avoid hydrolysis and formation of biuret in the stripping zone, it is essential that the residence time of the urea synthesis solution in the stripping zone be as short as possible. This is achieved by passing the solution along a wall in the form of a fast flowing film; the heat required is applied external to the wall and to accomplish this a vertical tubular heat exchanger is used in practice, through the shell or external side of which a heating medium flows, while the urea synthesis solution flows along the internal walls of the tubes in a direction counter-current to the ascending stripping gas. In order to avoid excess local heating of the urea synthesis solution and the hydrolysis and subsequent formation of biuret therefrom, it is necessary that the liquid to be stripped be applied as evenly as possible to the internal walls of the tubes. In view of this requirement, high demands are made on the distribution of the liquid over the interior of the tubes and one must use accurately dimensioned distributors. Further, care should also be taken that the stripping gas is evenly distributed over the internal areas of the tubes, which can be accomplished by providing the gas discharge ends of the tubes with identical orifices.

DETAILED DESCRIPTION OF THE INVENTION

We have found that it is possible for the ammonium carbamate present in the urea synthesis solution to be decomposed at a high pressure and for the gas mixture formed thereby to be expelled from the solution without the necessity to supply heat to this solution from an outside source. For, surprisingly, it has appeared that, calculated on the basis of the quantity of carbon dioxide supplied, the equilibrium conversion also continues to increase above 190°C, and that at higher temperatures the enthalpy or heat content per unit mass of the urea synthesis solution is sufficient to meet the heat demands made during the stripping treatment for the decomposition of the major portion of the ammonium carbamate present. Accordingly, this invention represents an improvement upon our earlier process.

Briefly stated, the present invention provides a process for preparing urea, in which ammonia and carbon dioxide are reacted in a synthesis zone at a suitable pressure and temperature, the urea synthesis solution thus formed is subjected to a stripping treatment by being countercurrently contacted with a gaseous medium such as carbon dioxide, and the gas mixture which forms during the stripping treatment is condensed to form ammonium carbamate which is recirculated to the urea synthesis zone. The improvement includes synthesizing at a pressure of at least 225 atm. and that the urea synthesis solution having an initial temperature of at least 205°C is contacted with the gaseous medium under mainly adiabatic conditions.

Maximum temperatures and pressures, which are of course interrelated, will depend to a large extent upon the operational conditions employed. Generally, the maximum for both parameters will be established by the process efficiency and will be adjusted accordingly; for example, appropriate adjustments are made as the efficiency declines when the pressure and/or temperature are increased. Usually, the pressure will not exceed about 600 atm. and the temperature will not be above 245°C, and although in theory these values may be exceeded, such operation will merely add to the cost of the process.

During the stripping treatment the liquid surface area in contact with the stripping gas should here, as in the prior process, be as large as possible in order that the mass transfer from the liquid phase to the gas phase proceed as rapidly and as completely as possible. According to one preferred embodiment of the process according to the present invention, the urea synthesis solution is introduced in the form of fine drops into a rising stream of the gaseous medium to increase the liquid surface area in contact with the stripping gas. According to another preferred embodiment of the process according to the present invention and in order to increase the liquid surface area, the urea synthesis solution is passed in the form of a thin film along a number of vertical or inclined planes of a plated stripping unit.

The heat required in the urea synthesis zone for the endothermic conversion of ammonium carbamate into urea may be obtained by condensing, according to known procedures, at least part of the gas mixture obtained during the stripping treatment in the synthesis zone and by directly utilizing in this way the heat liberated during the formation of ammonium carbamate. For this purpose and as an illustration, about 25–60% of the gas mixture formed during the stripping treatment is condensed in a separate condensation zone and the resulting mixture of gas and liquid is sent to the synthesis zone.

In comparison with known processes in which the synthesis solution is also subjected to a stripping treatment, the process according to the present invention involves several advantages. For instance, as a consequence of the higher pressure and temperature in the synthesis zone, the conversion of ammonium carbamate into urea proceeds at a higher rate, so that a larger conversion is achieved in a relatively short time. The specific reactor volume, that is, the reactor capacity per ton of urea to be produced, may be smaller. Condensation takes place at a higher pressure, so that heat of a higher temperature level may be recovered. As a result of the higher degree of conversion in the urea synthesis zone, less ammonium carbamate need be decomposed and less gas need be expelled. Hence, the size of the stripping unit may be smaller, for it is no longer determined by factors related to the heat transfer as in prior processes, but by quantities determining the mass transfer. Also, the design of the stripper may be simplified because instead of heat exchange tubes with liquid and gas distributors and the consequent uniform distribution problems thereof, liquid conveying devices of a less complicated nature may be used and in principle it is even possible to omit them entirely. Since the specific capacity of the various vessels is smaller, it is possible that at the same maximum dimensions, which depend on the transport facilities production units having larger capacities can be built than have so far, hence larger plants with larger production capacity. Other advantages attending the use of the improved process as described herein will be appreciated as the foregoing is intended to be merely an example or illustration of the potential advancements of the process.

The invention will now be further described and illustrated in the diagrammatic illustration.

Referring now to the attached figure, in synthesis autoclave 1, at a pressure of 225–500 atm. and a temperature of 195°–235°C, a urea synthesis solution is formed from ammonia supplied via line 2 and a mixture of gas and liquid supplied via line 3, which mixture contains ammonium carbamate, ammonia, carbon dioxide and water. The reaction conditions and the feed streams are adjusted such that the urea solution leaving the synthesis autoclave has a temperature of at least 205°C. Preferably, this temperature is in the range of 215° to 235°C. The temperature conditions in the synthesis autoclave will vary, provided that the discharged urea solution be of at least 205°C. The urea solution is introduced into the top part of column 5 via line 4, where it is counter-currently contacted with the carbon dioxide which is required for the urea synthesis, or another gas, for instance ammonia or ammonia synthesis gas, and which is led into the bottom part of column 5 via line 6. Heat is neither supplied nor withdrawn from column 5, so that the column operates under adiabatic conditions. The residence time of the urea synthesis solution in column 5 is kept as short as possible, preferably shorter than 10 seconds, in order to keep the hydrolysis of urea during the rectification within acceptable limits. The two demands, counter-current treatment and a short residence time, can be met with the aid of an irrigated wall column of enlarged internal surface area in which the solution to be rectified flows in the form of a thin film along a number of vertically arranged plates.

It is also possible to introduce the urea synthesis solution in a column without internal surface-expanding devices or baffles by spraying in the form of fine drops and to have these drops fall downward into a rising stream of stripping gas.

The solution collecting in the bottom part of column 5 after the stripping treatment is removed via line 7 and reducing valve 8 to a low-pressure stage not shown in the figure, where according to a known process as described in U.S. patent application Ser. No. 547,116, filed Mar. 23, 1966, the disclosure of which is hereby incorporated by reference, the ammonium carbamate values still present are decomposed and the liberated ammonia and carbon dioxide are separated off and condensed to form an ammonium carbamate solution and the aqueous urea solution is concentrated.

The remaining component is a gas mixture mainly consisting of ammonia, carbon dioxide and water vapor discharged from column 5 and led into condenser 10 via line 9 together with ammonia supplied via line 11 and ammonium carbamate solution supplied via line 12 from scrubber 13, in which with the aid of ammonium carbamate solution recirculated from the low-pressure stage via line 14, ammonia and carbon dioxide are removed from the gas mixture containing inert components which is discharged from synthesis autoclave 1.

In condenser 10 a portion of the gas mixture supplied is condensed such that a mixture of liquid and gas is obtained which still contains sufficient quantities of non-condensed ammonia and carbon dioxide to obtain urea synthesis solution of the desired final temperature of at least 205 °C after the mixture has been mixed with fresh ammonia supplied via line 2 and after condensation has been continued in synthesis autoclave 1. The process according to the present invention described above may be conducted and simplified by having the formation of the ammonium carbamate and the formation of urea therefrom take place completely in one device.

The process as described herein is not limited to one in which the stripping treatment is carried out at the same pressure as the urea synthesis for in principle, it is also possible to carry out the stripping treatment at a pressure lower than the synthesis pressure. However is practice the gas expelled during the lower pressure stripping treatment has to be compressed prior to being introduced into the condensation zone.

The present invention will be further illustrated by way of the following example wherein all parts and percentages are by weight unless otherwise indicated.

EXAMPLE

For preparation of 1,000 tons of urea a day which amounts to 41,665 kg/h, 23,610 kg/h of $NH_3$ and 30,555 kg/h of $CO_2$ are needed. Proceeding using process described on the basis of the attached diagram, 14,060 kg/h of $NH_3$ are supplied to synthesis autoclave 1 via line 2 and the remaining 9,550 kg/h to condenser 10 via line 11. Synthesis autoclave 1 is further supplied via line 3 with a mixture of gas and liquid having a temperature of 190° C whose gross composition is as follows:
 57,065 kg/h of $NH_3$
 53,105 kg/h of $CO_2$
 17,690 kg/h of $H_2O$ The pressure at which the urea synthesis, the stripping of the urea synthesis solution and the condensation of the gas mixture expelled during the stripping take place amounts to 360 kg/cm². The urea synthesis solution supplied to stripping column 5 has a temperature of 225° C. The composition is a follows:
 42,220 kg/h of $NH_3$
 17,440 kg/h of $CO_2$
 43,860 kg/h of urea
 30,550 kg/h of $H_2O$ This solution is introduced into the top part of column 5 which is provided with vertical plates along which the liquid flows downward as a thin film in countercurrent with 30,555 kg/h of $CO_2$ which has a temperature of 170° C and is introduced into the bottom part of the column. A solution is discharged from column 5 which in addition to 41,665 kg/h of urea and 27,590 kg/h of $H_2O$, contains 12,715 kg/h of $NH_3$ and 14,960 kg/h of $CO_2$ and has a temperature of 190° C. From the top of column 5 a gas mixture is discharged consisting of:
 30,750 kg/h of $NH_3$
 34,645 kg/h of $CO_2$
 2,300 kg/h of $H_2O$,
which mixture is led into condenser 10.

The dilute ammonium carbamate solution which is led from the low-pressure stage to scrubber 13 forms a solution with the components therein absorbed from the purge gas mixture, which solution contains
 16,765 kg/h of $NH_3$
 18,460 kg/h of $CO_2$
 15,390 kg/h of $H_2O$,
and which is also leg into condenser 10. In this condenser 5 tons/h of 8 atm. steam are formed.

We claim:

1. In a continuous process for the preparation of urea wherein $NH_3$ and $CO_2$ are reacted at elevated temperature and pressure in a synthesis zone to continuously provide ammonium carbamate, thereafter converting the ammonium carbamate into a urea solution containing unconverted ammonium carbamate and stripping the carbamate from said solution in a stripping zone by decomposing the carbamate by continuously contacting said solution with a stripping gas at a temperature of about 180° to at most 200° C. and under a pressure of about 125 to at most 200 atm. continuously in said stripping zone, said urea synthesis zone and stripping zone being operated under substantially the same pressure, expelling the resulting $NH_3$, $CO_2$ and $H_2O$ from said stripping zone, condensing the resulting mixture of stripping gas and gases expelled from said urea solution after addition of further $NH_3$ or $CO_2$ to form a carbamate solution, and returning the thus formed carbamate solution to said urea synthesis zone for further urea synthesis, the improvement comprising conducting said urea synthesis and stripping zone at a pressure of at least 225 atm., and contacting said urea solution with said stripping gas at an initial temperature of at least 205° C, said stripping step occurring under substantially adiabatic conditions devoid of the addition of heat to said stripping zone.

2. The process according to claim 1 wherein said stripping is conducted by spraying said urea synthesis solution in the form of fine droplets into the ascending stripping gas.

3. The process according to claim 1 wherein said stripping is conducted by downwardly flowing said urea synthesis solution in a thin film over a number of vertical or inclined planes of said stripping zone while contacting the ascending gaseous medium.

4. The process according to claim 1 wherein the said initial temperature is in the range from about 215° to about 235 °C.

* * * * *